(12) United States Patent
Nering et al.

(10) Patent No.: US 10,772,653 B2
(45) Date of Patent: Sep. 15, 2020

(54) LAPROSCOPIC INSTRUMENT DEPTH STOP

(71) Applicants: Robert Nering, Stockton, NJ (US);
Elias N. Shalhoub, Cranston, RI (US)

(72) Inventors: Robert Nering, Stockton, NJ (US);
Elias N. Shalhoub, Cranston, RI (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/798,664

(22) Filed: Mar. 13, 2013

(65) Prior Publication Data
US 2014/0276907 A1    Sep. 18, 2014

(51) Int. Cl.
*A61B 17/32* (2006.01)
*A61B 17/34* (2006.01)
*A61B 90/00* (2016.01)

(52) U.S. Cl.
CPC .......... *A61B 17/32002* (2013.01); *A61B 2017/320024* (2013.01); *A61B 2017/3492* (2013.01); *A61B 2090/033* (2016.02)

(58) Field of Classification Search
CPC .......... A61B 5/15019; A61B 17/32002; A61B 2090/033; A61B 2017/320024; A61B 2017/3492
See application file for complete search history.

(56) References Cited

U.S. PATENT DOCUMENTS

| | | | |
|---|---|---|---|
| 4,632,597 A * | 12/1986 | Clausen et al. | F16B 2/04 403/351 |
| 5,147,164 A | 9/1992 | Fraver | |
| 5,217,441 A | 6/1993 | Shichman | |
| 5,279,575 A | 1/1994 | Sugarbaker | |
| 5,417,511 A * | 5/1995 | Warden | 403/109.5 |
| 5,694,695 A * | 12/1997 | Lund | B25G 1/04 15/144.4 |
| 5,787,590 A * | 8/1998 | D'Alessandro, Sr. | A01G 3/053 16/429 |
| 6,524,306 B1 | 2/2003 | Hennig | |
| 6,951,562 B2 | 10/2005 | Zwirnmann | |
| 7,141,074 B2 | 11/2006 | Fanger et al. | |
| 7,513,722 B2 | 4/2009 | Greenberg et al. | |
| 7,730,628 B2 | 6/2010 | Hoffman | |
| 2007/0210018 A1 | 9/2007 | Wallwiener et al. | |
| 2008/0065129 A1 | 3/2008 | Batchelor et al. | |
| 2009/0158875 A1* | 6/2009 | Crooks | F16H 55/12 74/436 |
| 2010/0063529 A1 | 3/2010 | Buser et al. | |

(Continued)

FOREIGN PATENT DOCUMENTS

EP    2147654 A1    1/2010

*Primary Examiner* — Elizabeth Houston
*Assistant Examiner* — Michael G Mendoza

(57) ABSTRACT

Disclosed is an infinitely adjustable depth stop for a laparascopic instrument having a shaft, the depth stop including a first component having a first annular space adapted to allow the shaft to be fitted therethrough. The first annular space has a reducible diameter and an interference surface against which the shaft may be fitted. Upon reduction of the reducible diameter, the interference surface frictionally engages the shaft to arrest relative movement of the depth stop along the shaft. The frictional engagement may be along a curve, a spiral curve, or an area. Means are also provided to reopen the reducible diameter to release the depth stop.

18 Claims, 22 Drawing Sheets

(56) References Cited

U.S. PATENT DOCUMENTS

2010/0210147 A1* 8/2010 Hauser .................. H01R 13/24
                                                        439/660
2010/0273342 A1* 10/2010 Hankins ............... H01R 13/625
                                                         439/332

* cited by examiner

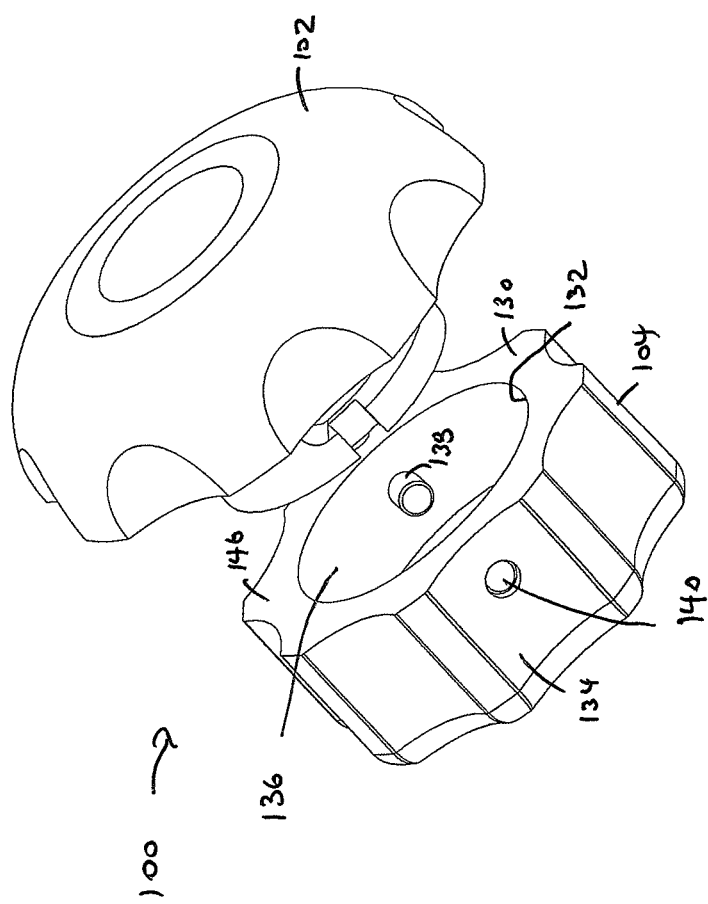

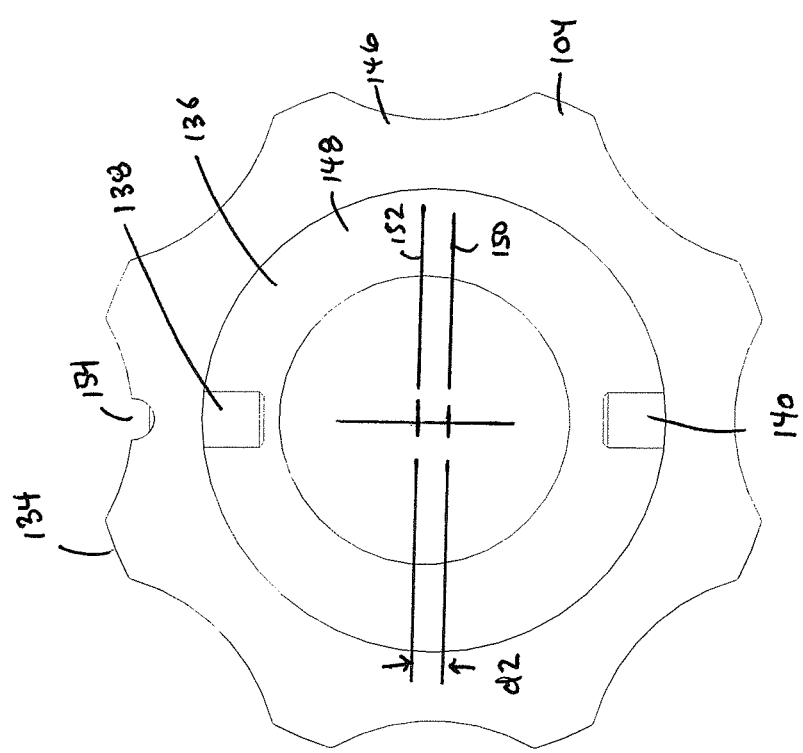

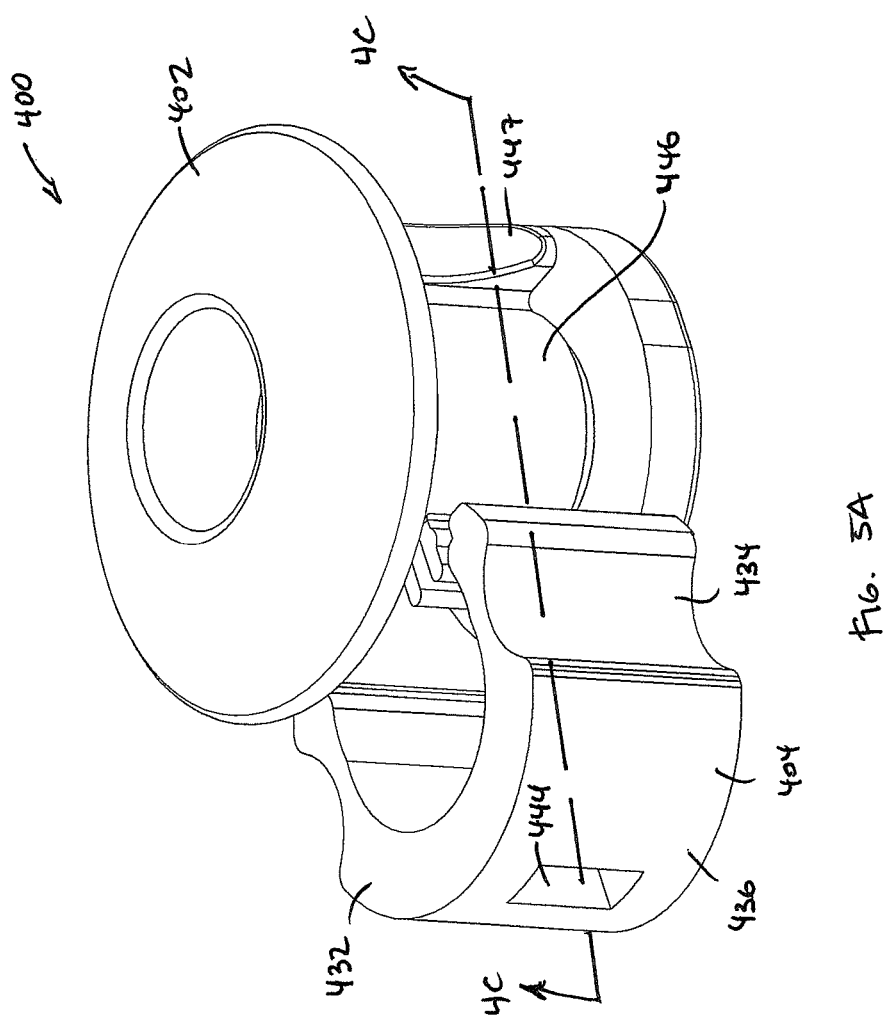

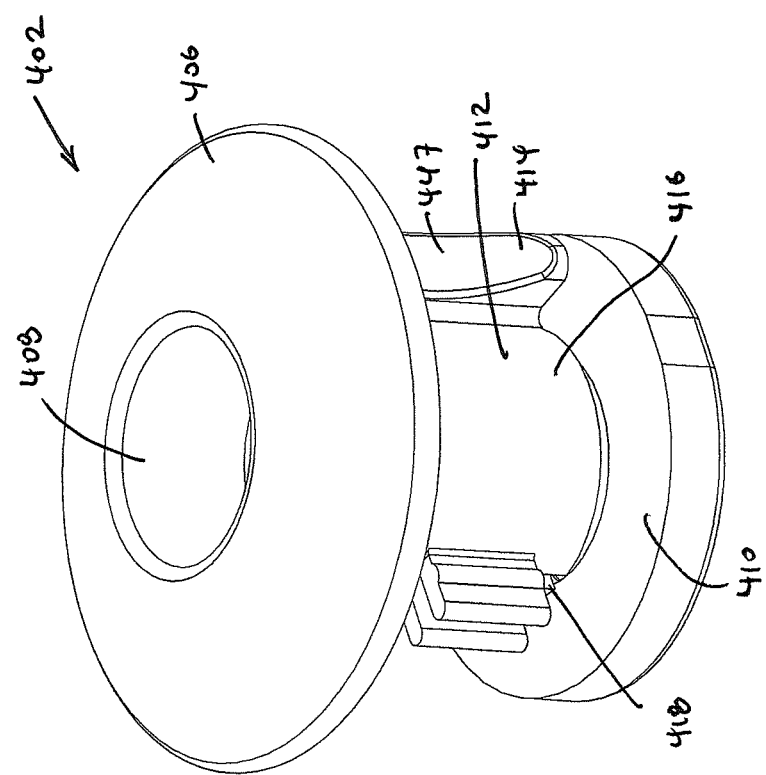

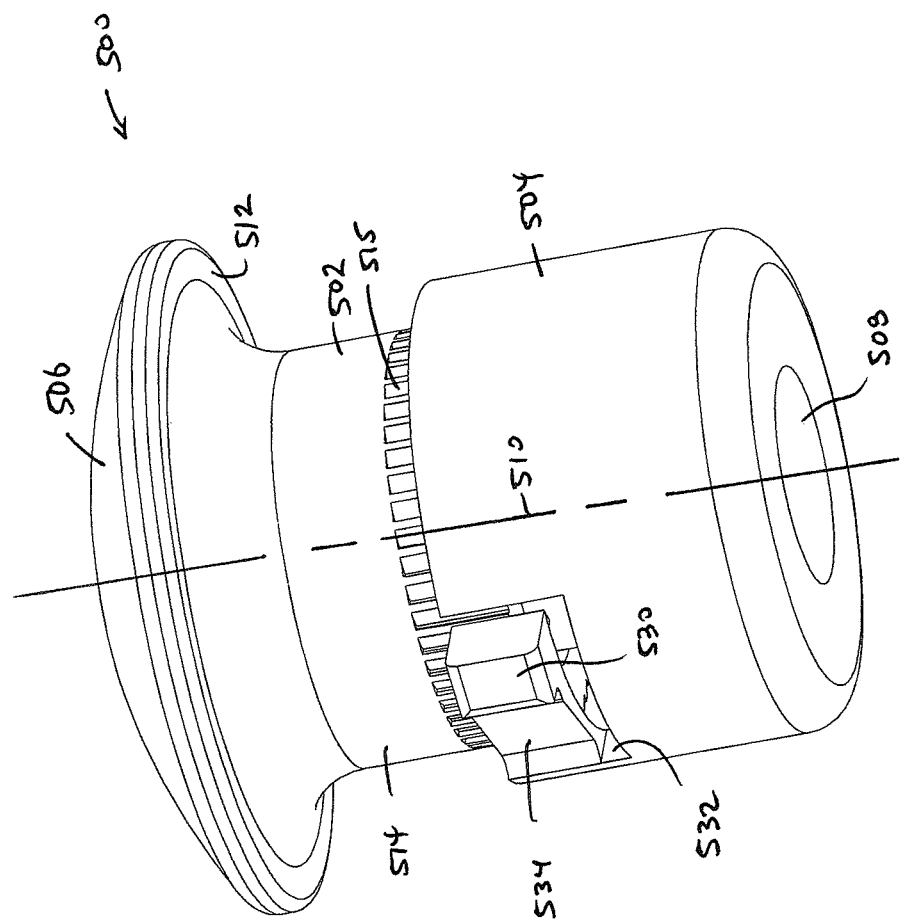

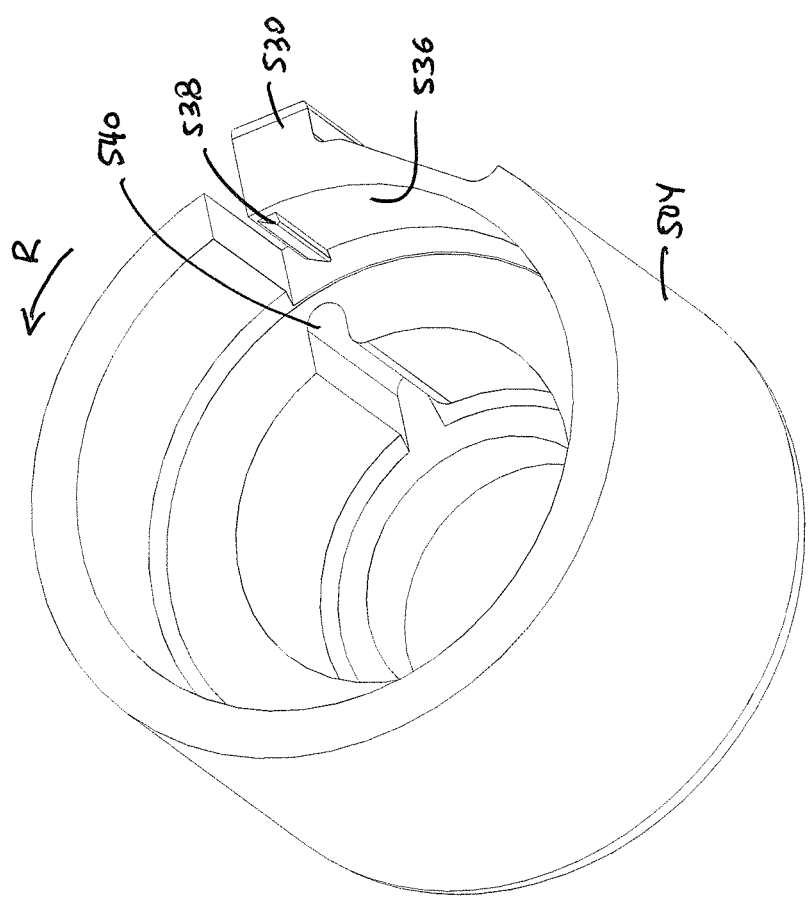

LAPROSCOPIC INSTRUMENT DEPTH STOP

BACKGROUND OF THE INVENTION

The present invention relates to laparascopic instrument depth stops, particularly morcellator depth stops.

Morcellating devices are conventionally utilized for removing tissue from patients during a laparoscopic procedure. Examples of such tissue may be uterine fibroids or even an entire uterus. In some instances, it is desirable to limit the depth of penetration of the morcellating device beneath the skin of a patient to prevent insertion of the mocellating portion of the device beyond the compromised tissue and into healthy tissue below.

One known method of limiting the depth of penetration is to provide a sliding collar that may be slid up and down the shaft of a morcellating device and locked into place with a locking set screw. Another method includes spacers placed in series on the shaft of the morcellating device. In these devices, the sliding collar or spacers abuts the exterior skin of a patient and serve to restrict the depth in which the shaft may penetrate the body.

BRIEF SUMMARY OF THE INVENTION

Although well received, these methods have proven to be insufficient for the delicate equipment and in the modern operating arena. In the sliding collar example, the locking screw has proven to be difficult to secure with a gloved hand. Moreover, torqueing of the screw creates a point load that can easily damage the morcellator shaft. In the stacked spacer example, depth adjustability is naturally limited by the number and dimensions of the spacers available. It is therefore very difficult to provide a stop at precisely the necessary depth for a particular patient.

The present invention provides for laparascopic depth stops that are attachable to a laparascopic instrument shaft, such as a morcellator shaft, where the depth stops can be adjusted and securely positioned on the shaft to enable infinitely variable positioning with heretofore unknown ease of use. The laparascopic depth stops described herein also provide the capability of being secured to the morcellator without damaging the morcellator shaft. Principally, the shaft is protected from damage because the forces acted upon it by the inventive devices are non-point load forces, and instead act along a curve, spiral curve, or area.

In accordance with one embodiment of the invention, there is provided a depth stop for a laparascopic instrument having a shaft, where the depth stop comprises a first component having a first annular space adapted to allow the shaft to be fitted therethrough, and a second component adapted to be connected to the first component, the second component having a second annular space adapted to allow the shaft to be fitted therethrough. The first annular space and the second annular space form a combined annular space having a first cross sectional area. When the first component is moved relative to the second component the combined annular space reduces to a second cross sectional area less than the first cross sectional area to impart a force on the shaft, the force capable of arresting relative movement of the depth stop along the shaft.

The movement may be by rotation.

The reduction in combined annular space may be created by eccentric alignment of the first annular space and second annular space relative to each other. If so provided, the first component may comprise a handle with a cylindrical portion extending therefrom, the cylindrical portion having an exterior recess. The second component may include a cylindrical well adapted to accept the cylindrical portion of the first component, the cylindrical well having an interior extension adapted to fit within the recess when the first component and the second component are connected.

The reduction in annular space may be created by tapering of the first annular space. If so provided, the first component may comprise a tapered section and the second component may comprise a collet that conforms to the geometry of the tapered section. The first component and the second component may be threaded together with threads, whereby rotation of the first component and second component relative to each other moves the collet with respect to the tapered section.

The reduction in annular space may be created by rotation of a stop lever about a point outside the cross sectional area of the shaft. The depth stop may further comprise a spring, the spring imparting a force on the stop lever. The stop lever includes a cylindrical section between a first tab and second tab.

The second component may be a helical coil. The first component may further comprise a series of recesses, the depth stop further comprising a third component, the third component including a ramp adapted to ratchet with the series of recesses. The depth stop may further comprise a release button adapted to release the ramp from the series of recesses.

In accordance with a further embodiment, there is provided a depth stop for a laparascopic instrument having a shaft, where the depth stop comprises a first component having a first annular space with a first cross sectional area adapted to allow the shaft to be fitted therethrough, and a second component adapted to be fitted over portions of the first component to reduce the first annular space to a second cross sectional area less than the first cross sectional area.

The second component may be fitted over the first component by moving the second component a direction perpendicular to the longitudinal axis of the shaft.

The second component may be a clip having first and second legs connected by a connector member.

In accordance with a further embodiment of the invention, there is provided a depth stop for a laparascopic instrument having a shaft, where the depth stop comprises a first component having a first annular space adapted to allow the shaft to be fitted therethrough. The first annular space has a reducible diameter and an interference surface against which the shaft may be fitted. Upon reduction of the reducible diameter, the interference surface frictionally engages the shaft to arrest relative movement of the depth stop along the shaft.

The frictional engagement may be along a curve. The curve may be a spiral curve.

The frictional engagement may form an area.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof, will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

With respect to the drawings,

FIG. 1B depicts an alternate embodiment of a conventional depth stop;

FIG. 2B depicts a second perspective view of the depth stop of FIG. 2A;

FIG. 2D depicts a top view of the female component forming a portion of the depth stop of FIG. 2A;

FIG. 5A depicts a perspective view of a depth stop in accordance with a fourth embodiment of the present invention;

FIG. 5B depicts a perspective view of the base component of the depth stop of FIG. 5A;

FIG. 6A depicts a perspective view of a depth stop in accordance with a fifth embodiment of the present invention;

FIG. 6E depicts a perspective view of the outer portion of the depth stop of FIG. 6A.

DETAILED DESCRIPTION

Figure 1A:
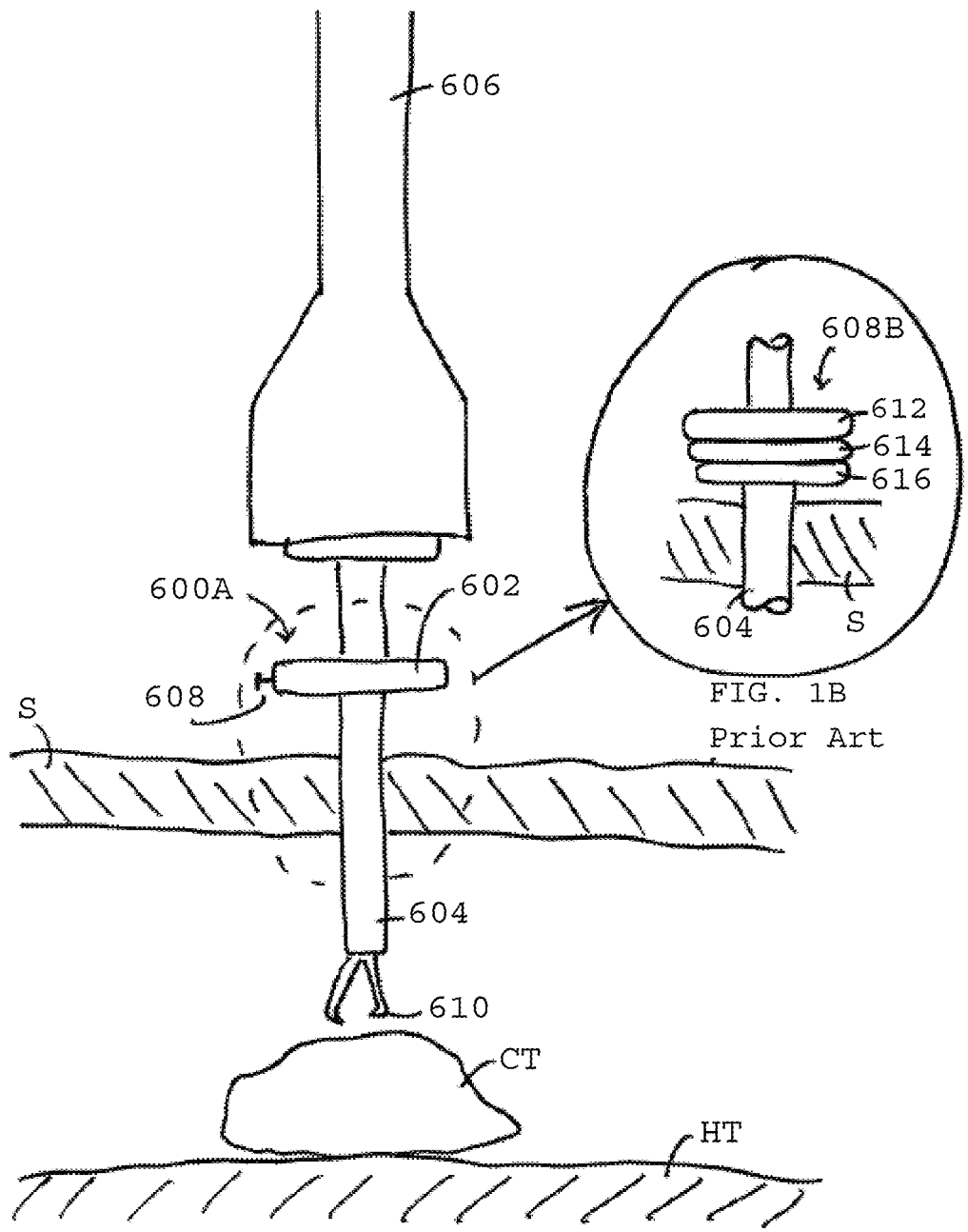
FIG. 1A depicts a conventional depth stop in use on a surgical morcellating device.

In the following are described the preferred embodiments of the laparascopic instrument depth stop of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose. Where like elements have been depicted in multiple embodiments, identical reference numerals have been used in the multiple embodiments for ease of understanding.

As discussed above, the invention features laparascopic depth stops that are attachable to laparascopic devices. For ease of discussion, a morcellator will be used as a representative device. However, other laparascopic devices are to be considered within the context of this disclosure.

The present disclosure therefore provides for depth stops for a morcellator having a shaft, where the depth stops can be adjusted with infinitely variable positioning and then secured to the shaft. The laparascopic depth stops described herein also provide the capability of being secured to the morcellator without damaging its shaft by applying force to the shaft in a form other than a point load. For example, the forces applied may be along a curve, spiral, or within an area.

As discussed above, conventional depth stops are known. FIG. 1A discloses one such conventional depth stop 600A generally comprising a sliding collar 602 that may slide along the shaft 604 of a morcellator 606, or other laparascopic device. The sliding collar 602 includes a locking screw 608 that may be tightened to lock the sliding collar against the shaft 604. Thus, when the shaft 604 of the morcellator 606 is inserted through the skin S of a patient, its end 610 may be prevented from extending beyond compromised tissue CT to be removed and into healthy tissue HT.

In so locking the device of FIG. 1A, it will be appreciated that the forces acting on the shaft 604 by virtue of the locking screw 608 are point forces. No matter how much care is taken by the surgeon in securing the sliding collar 602, these point forces may damage the delicate shaft 604 of the surgical tool.

FIG. 1B depicts an alternative conventional system. Here, the depth stop 608B generally comprises a series of spacers 612, 614, 616 that may be stacked to limit the excursion of the shaft 604 into the skin S. The number of spacers and the size of the spacers may be varied as required. Nevertheless, there are only a reasonable number of different size spacers to choose from, and the depth stop is therefore not infinitely variable.

Generally speaking, the depth stops of the present invention provide for curve, spiral, or area contact between portions of the depth stop and the morcellator shaft rather than point contact. These configurations help to equalize or counteract forces acting on the morcellator shaft while also minimizing the impact of such forces resulting in both improved functionality and reduced risk of damaging the morcellator shaft. Additionally, the depth stops of the present invention provide infinitely variable depth control by being adjustable in an infinite number of positions.

Figure 2A:
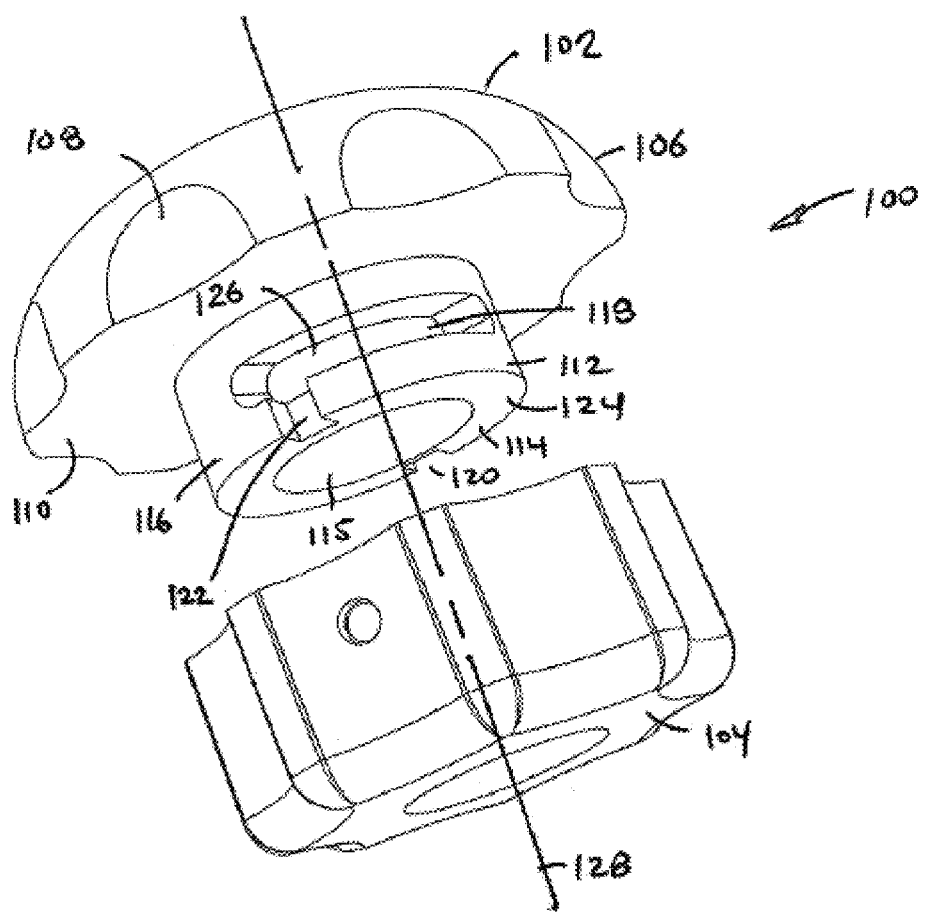
FIG. 2A depicts a perspective view of a depth stop in accordance with a first embodiment of the present invention.

In accordance with one embodiment, presented initially in a first perspective view in FIG. 2A, a depth stop 100 comprises a male component 102 and a female component 104. As will be discussed, the male component 102 and female component 104 engage each other and may be turned relative to each other to offset eccentric lumens that engage the shaft of a morcellator to lock the depth stop 100 in place.

The male component 102 comprises a handle 106 which in the embodiment shown is generally formed in the shape of a mushroom. Other configurations that easily fit within the grasp of a gloved surgeon are also contemplated. Moreover, the handle may be knurled or may include depressions 108, as shown, to aid in tactile feel and grip.

Extending from a central location of the bottom portion 110 of the handle 106 is a male connector 112. The male connector 112 is configured as an open cylindrical structure with an annular wall 114 forming an annular space 115. Formed in the generally smooth outer portions 116 of the annular wall 114 are a pair of recesses 118, 120. As best shown in FIG. 2A with respect to recess 118, the recesses 118, 120 each include a first portion 122 extending through the annular wall 114 to the termination 124 thereof. In turn, the first portion 122 extends in the opposite direction into a second portion 126 generally configured transverse to the first portion and extending partially around the central axis 128 of the male component 102 and particularly the male connector 112.

FIG. 2B depicts the depth stop 100 in a second perspective view highlighting the female component 104. As shown, the female component 104 is generally configured as a circular component forming an annular ring 130. The annular ring 130 forms a well, is generally smooth on its interior portion 132, and may be knurled or otherwise shaped on its outer portion 134 to facilitate handling by a gloved surgeon. As shown in FIG. 2B, the outer portion 134 is preferably scalloped. Extending from the interior portion 132 into the annular space 136 provided by the annular ring 130 are a pair of extensions 138, 140. The extensions 138, 140 may be formed as part of the female component 104 or may be formed as separate pins that are fitted in apertures of the female component and affixed therein.

In the embodiment shown, the extensions 138, 140 are tubular but it will be appreciated that the extensions may be configured as other shapes and configurations provided that such shapes or configurations are adapted to fit within the recess 118 of the male connector 112. It will also be appreciated that the male component 102 and female component 104 may be fitted together by positioning the extensions 138, 140 first into the first portions 122 (and the other corresponding first portion) of the recesses 118, 120 and then into the second portions 126 (and the other corresponding second portion). Upon rotation of the male component 102 relative to the female component, the extensions 138, 140 will travel through the second portions 126 (and the other corresponding second portion) to lock the two components together.

Figure 2C:
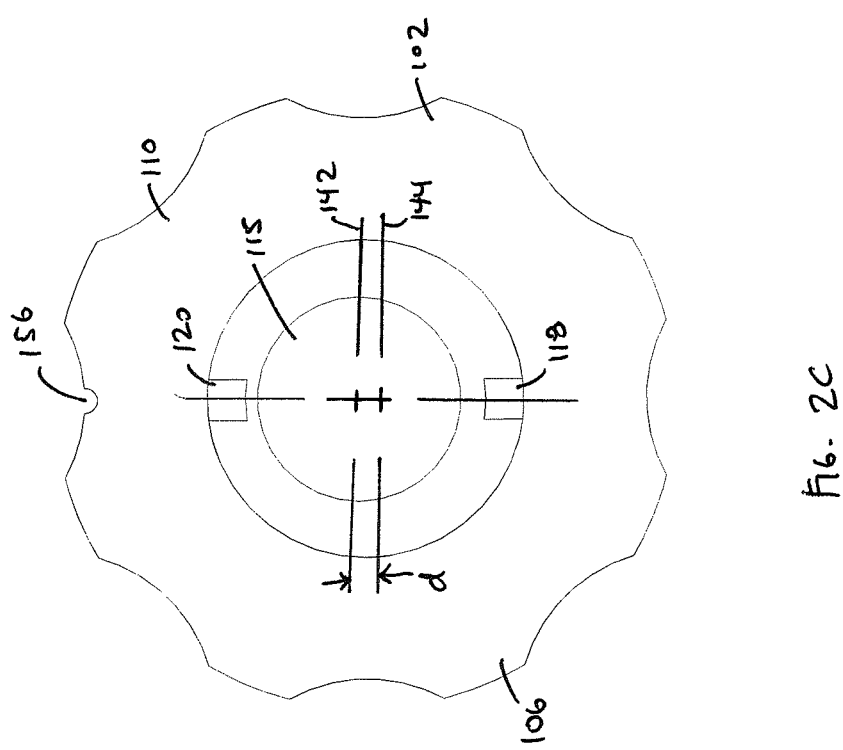
FIG. 2C depicts a bottom view of the male component forming a portion of the depth stop of FIG. 2A.

FIG. 2C depicts a bottom view of the male component 102. Highlighted for reference are the bottom portion 110 of the handle 106 and male connector 112. From this view, it will be appreciated that the geometric centerline 142 of the annular wall is offset from the geometric centerline 144 of the outer portion 116 of the male connector 112 by a distance "d." Distance "d" is preferably 0.20" and the exact tolerance would depend on the materials used and the tolerance range of the instrument. This offset creates a first eccentricity.

A second eccentricity is shown in FIG. 2D, a top view of the female component 104. The eccentricity can be seen by examination of the apertures formed by the top portion 146 of the annular ring 120, which is also shown in FIG. 2B, versus the bottom wall 148 within the annular space 136. Here, the geometric centerline 150 of the top portion 146 (and the outer portion 134) is offset a distance "d2" from the geometric centerline 152 of the bottom wall 148. Notably, the female component 104 includes a notch 154 on its outer wall aligning with the smaller annular diameter of the female component while the male component also includes a similar notch 156 (FIG. 2C) aligning with the smaller annular diameter thereof. When the two notches 154, 156 are aligned, so too are the extensions 138, 140 and the recesses 118, 120.

A morcellator shaft may be positioned through the annular space 115 of the male component and the annular space 136 of the female component 104 with the two components connected and the notches 154, 156 aligned. The depth stop 100 may then be moved up or down the morcellator shaft to a desired position, whereby the surgeon may rotate one or both of the male component 102 and female component 104 to provide for a shift in the two annular spaces 115, 136. This shift reduces the overall cross sectional area of the combined annular space. It will be appreciated that the annular spaces 115, 136 are sized such that this shift and reduction in size locks the depth stop 100 against the morcellator shaft by virtue of friction alone. To unsecure the depth stop 100, the surgeon merely has to rotate the two components in the opposite direction. If it is desired to take the two components apart, the surgeon rotates in the opposite direction the full excursion permitted and pulls the components apart as the extensions 138, 140 are removed from the recesses 118, 120.

Figure 2E:
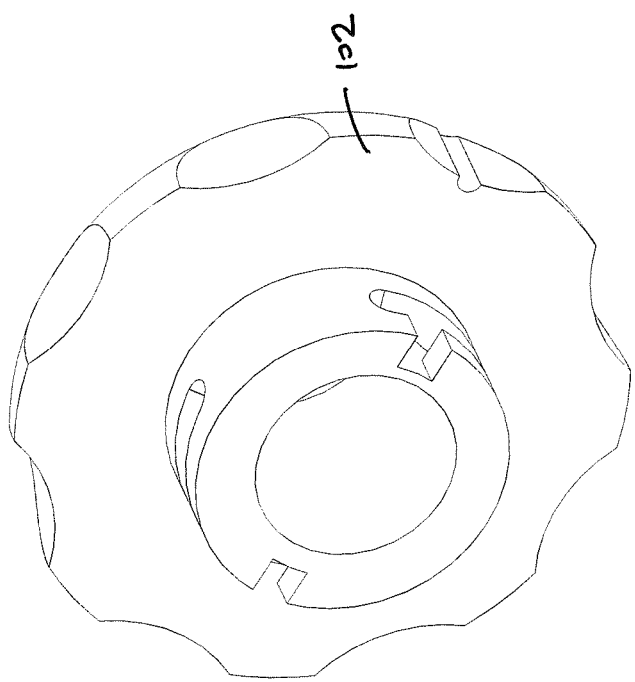
FIG. 2E depicts a perspective view of the male component of FIG. 2C.
Figure 2F:
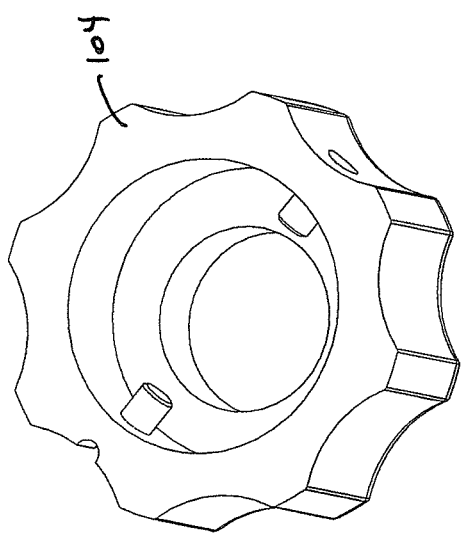
FIG. 2F depicts a perspective view of the female component of FIG. 2D.

For clarity, FIGS. 2E and 2F are also provided, with FIG. 2E being a further perspective view of the male component 102 and FIG. 2F being a further perspective view of the female component 104.

Figure 3A:
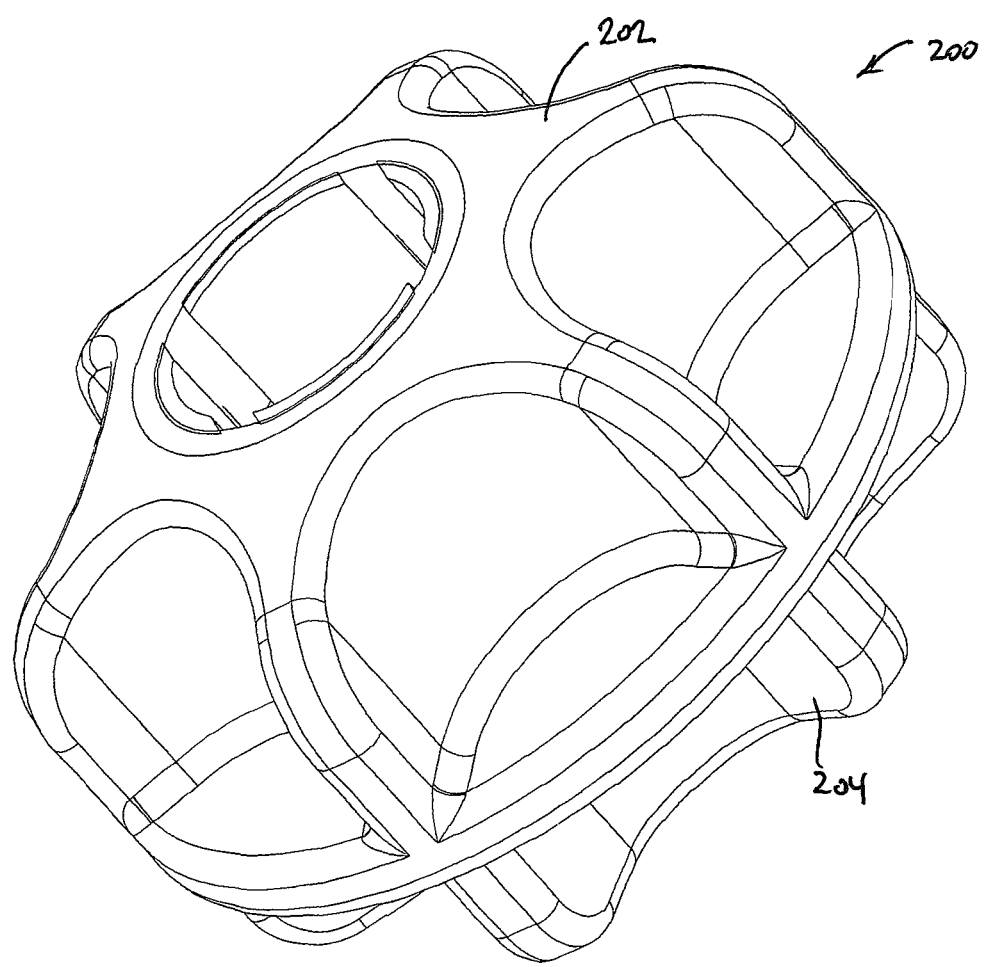
FIG. 3A depicts a depth stop in accordance with a second embodiment of the present invention.

A second embodiment of the invention is provided in FIG. 3A in the form of depth stop 200. Depth stop 200 comprises two major components, an outer component 202 and an inner component 204. As shown in FIG. 3A, the inner component and outer component may be fitted together.

Figure 3B:
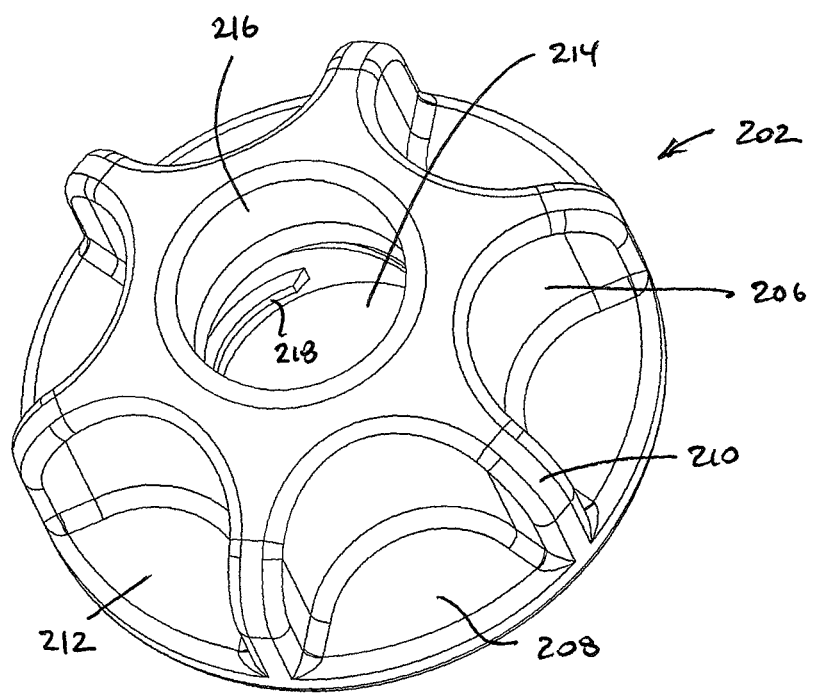
FIG. 3B depicts a perspective view of the outer component of the depth stop of FIG. 3A.

A perspective view of the outer component 102 is shown in FIG. 3B. As shown, the outer component comprises a gripping portion 206 and a base portion 208. The base portion 208 is generally round while the gripping portion 206 extends outwardly therefrom with a series of fins 210. The fins 210 are separated by scalloped sections 212 to enable the gloved hand of a surgeon to interact with the outer component 202. Of course, other configurations are possible.

Extending through a central portion of the outer component 202 is a lumen 214 having an inner wall 216. The inner wall 216 of the lumen includes threads 218. It will be appreciated that the inner wall 216 of the lumen 214 tapers from a first diameter near the base 208 to a smaller second diameter near the upper extent of the fins 210.

Figure 3C:
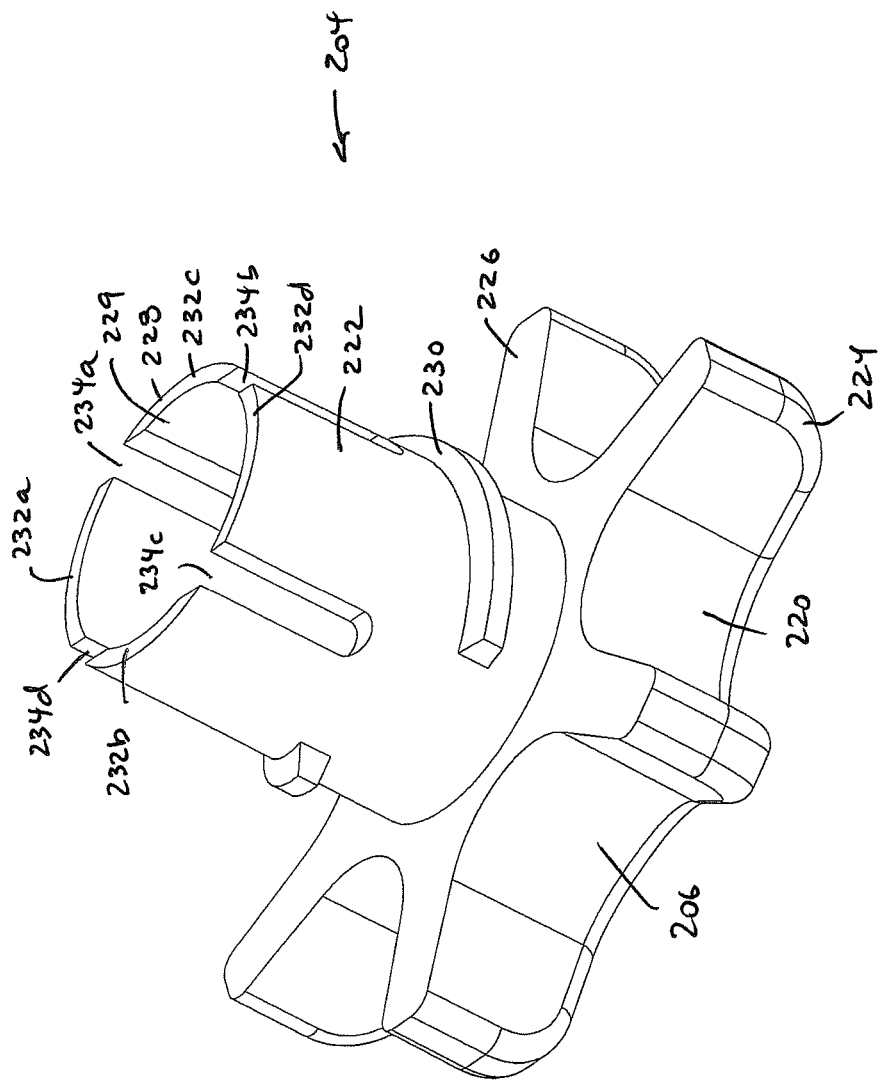
FIG. 3C depicts a perspective view of the inner component of the depth stop of FIG. 3A.

FIG. 3C depicts a perspective view of the inner component 204 of the depth stop 200. The inner component 204 comprises a handle section 220 and a collet section 222. The handle section 220 is configured with arrayed fins 224 separated by scalloped sections 226 to aid with a surgeon's grasping of the depth stop 202.

The collet section 222 extends outwardly from the base 226 of the handle section 220 toward a collet section terminus 228. It will be appreciated that the collet section 222 is sized and configured to fit within the lumen 214 of the outer component 202 and includes threads 230 for mating with the threads 218 of the outer section. When so engaged, the outer component 202 and inner component 204 may be rotated relative to each other to advance the inner component, and specifically the collet section 222, further into the lumen 214 of the outer component.

The collet section is tubular and includes a lumen 229 therethrough. At the terminus 228 of the collet section 222 are collets 232a, 232b, 232c, 232d. Although four such collets are shown, there may be as few as one or more than four. As the collet section 222 is advanced through the lumen 214 of the outer component 202, the collets 232a, 232b, 232c, 232d are squeezed together into the spaces 234a, 234b, 234c, 234d there between by virtue of the tapered inner wall 216

It will be appreciated that when the lumen 214 of the outer component 202 and the lumen 229 of the collet section 222 of the inner component 204 are threaded through the shaft of a morcellator, the components are free to slide up and down thereon. The inner and outer components 202, 204 are sized and configured such that when the inner component is threaded into the outer component, and the two components are rotated relative to each other, the collets 232a, 232b, 232c, 232d will squeeze together by virtue of the tapered inner wall 216 of the lumen 214 to squeeze the morcellator shaft and affix the depth stop 200 thereon. Relative rotation in the opposite direction serves to unfix the two depth stop 200 from the shaft by releasing the collets 232a, 232b, 232c, 232d.

It will be appreciated that the depth stop 200 may be sized and configured such that the collets 232a, 232b, 232c, 232d provide effective force on the morcellator shaft without damaging the shaft. Also, the thread pitch may be engineered to limit the rotation necessary to achieve such effective force, or may be engineered to permit finer control by requiring a greater degree of rotation to achieve the effective force.

Figure 4A:
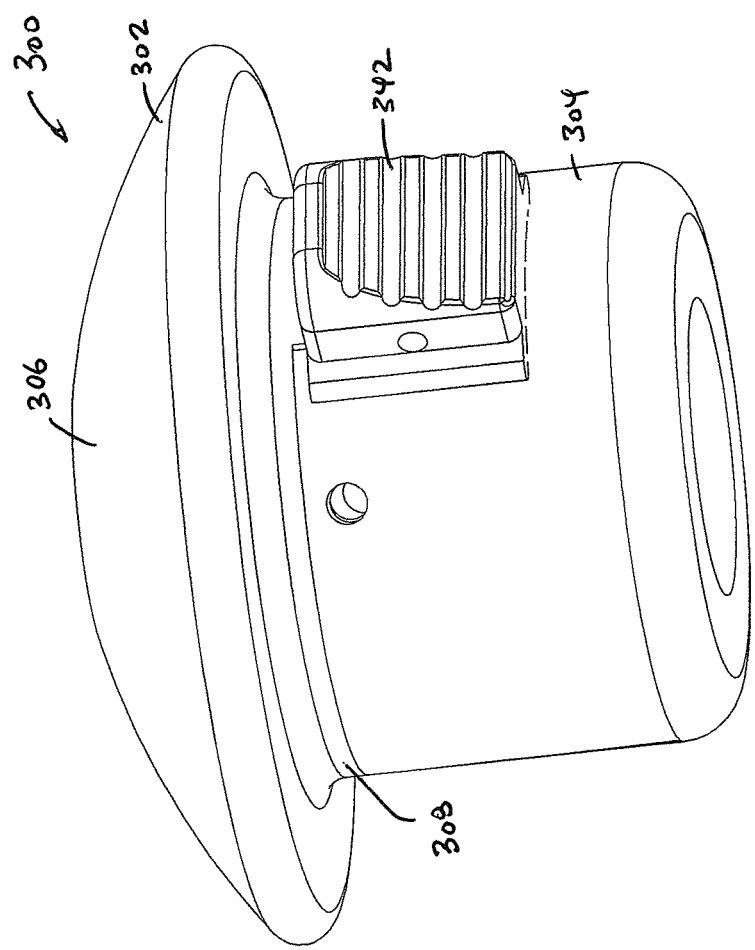
FIG. 4A depicts a perspective view of a depth stop in accordance with a third embodiment of the present invention.

A third embodiment of the invention is first depicted in FIG. 4A as depth stop 300. Depth stop 300 comprises a first section 302 and a second section 304. The first section 302 is generally mushroom-shaped and includes a mushroom cap 306 and base section 308. The second section 304 is generally cylindrical and connects with the base section 308 of the first section 302.

Figure 4B:
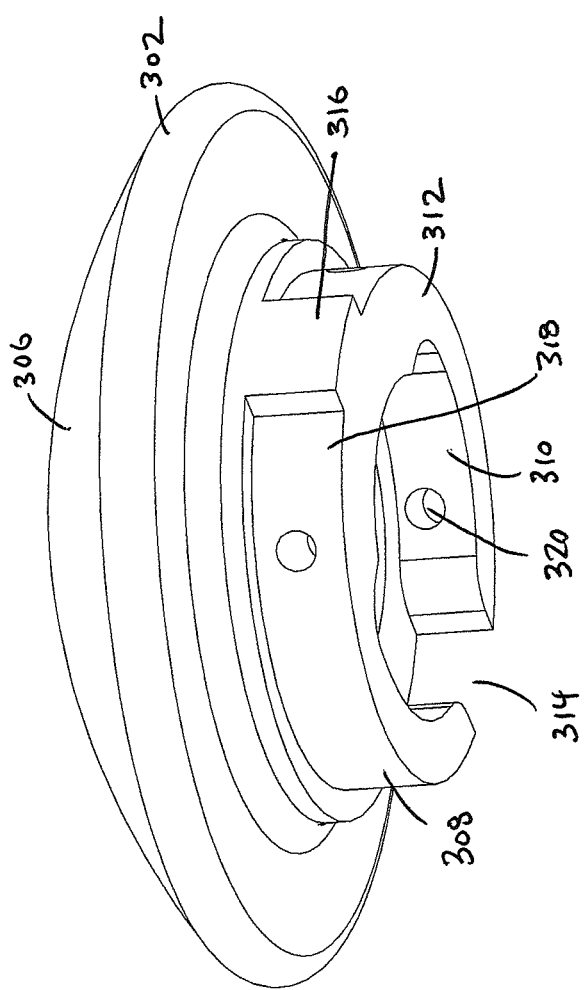
FIG. 4B depicts a perspective view of a first section of the depth stop of FIG. 4A.

The first section 302 is shown in greater detail in FIG. 4B. Here, it can be seen that the base section 308 comprises a plurality of separate sections, including an open cylindrical section 310. The open cylindrical section 310 includes a partial cylinder section 312 with an open section 314. Opposite the open section 314 is a plug 316 extending from the exterior wall 318 of the open cylindrical section 310. Lastly, the open cylindrical section also includes a plurality of apertures 320.

Figure 4C:
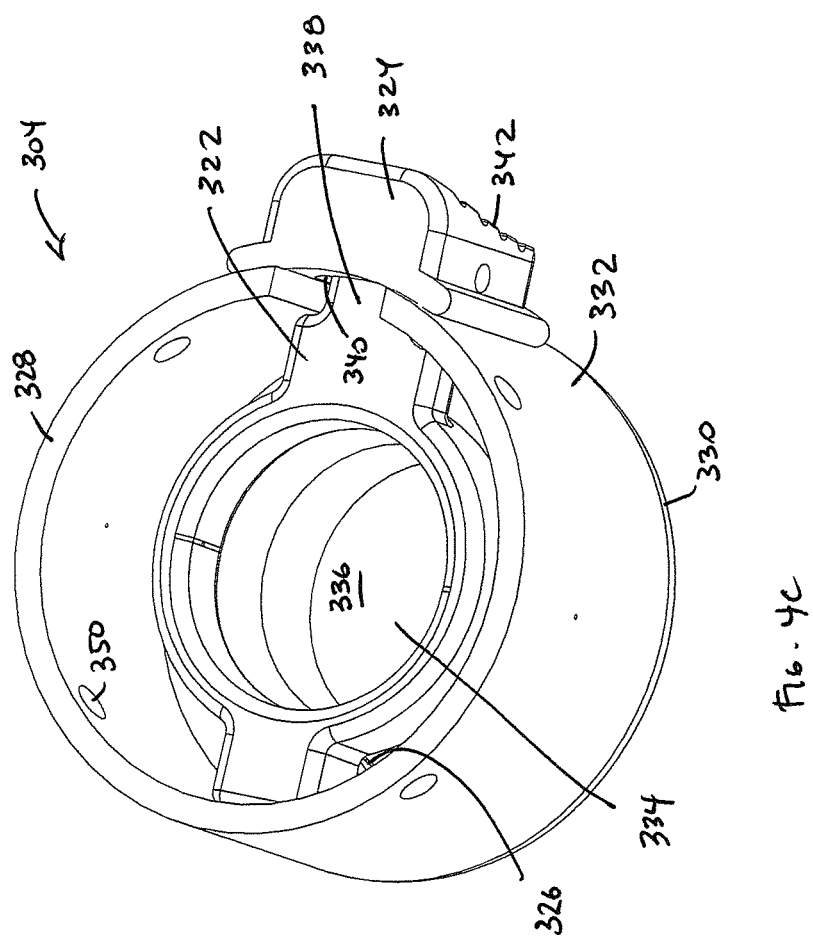
FIG. 4C depicts a perspective view of the second section of the depth stop of FIG. 4A.

FIG. 4C depicts a top perspective view of the second section 304. The second section 304 comprises several components, including a stop lever 322, actuator slide 324, spring 326, and a cylindrical body 328. The cylindrical body 328 generally comprises a base 330 and a cylindrical upstanding wall 332 extending therefrom. The cylindrical upstanding wall 332 includes an annular space 334 within its confines. It will also be appreciated that the base 330 includes an aperture 336.

The upstanding wall 332 includes an open section 338 adjacent to which is the actuator slide 324. The actuator slide 324 includes an opening 340 facing inward relative to the second section 304 and ribs 342 facing outward. The ribs 342 facilitate tactical feel of a gloved surgeon.

The stop lever 322 extends across the upstanding wall 332 from a portion opposite the open section 338, where it connects to spring 326, to the open section 338. In turn, the spring 326 connects between the stop lever 322 and the base 330 of the cylindrical body 328.

Figure 4D:
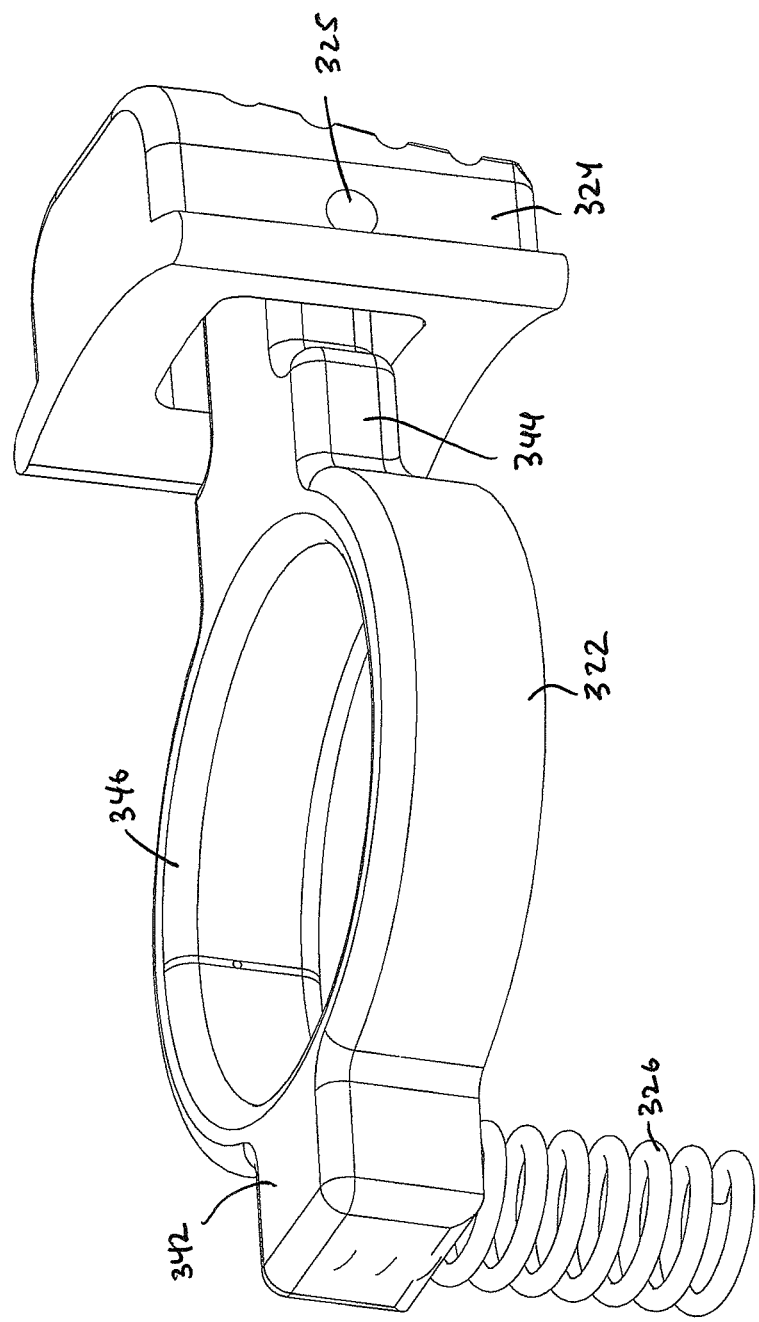
FIG. 4D depicts a perspective view of select components of the second section of the depth stop of FIG. 4A.

The configuration of the stop lever 322, spring 326, and slide 324 are shown in FIG. 4D. In FIG. 4D, it is shown that the stop lever 322 includes a spring tab 342 on a first side for connecting to the spring 326 and a slide tab 344 on a second side for connecting to the slide 324. Between the spring tab 342 and the slide tab 344 is a cylindrical section 346. In the standard configuration, it will be appreciated that the stop lever 322 is parallel to the base 330 of the cylindrical body 328 such that the lumen 348 of the cylindrical section 346 presents its greatest cross sectional area to a morcellator shaft extending through the cylindrical body. The connection between the spring tab 342 and spring 326 may be a pressure fit within an aperture (not shown) of the 342, or other means. The connection between the slide tab 344 and slide 324 is preferably by way of a pin 325.

It is also noted that the cylindrical body 332 includes a plurality of apertures 350, generally corresponding to the size and configuration of the apertures 320 of the first section 302. Thus, when the first section 302 and second section 304 of the depth stop 300 are brought together, pins (not shown) may be driven through the aligned apertures 320, 350 to connect the two members. So connected, it will be appreciated that a shaft of a morcellator may be threaded through the aperture of the first member (not shown, but configured at the upper extremity of the mushroom head 306), the stop lever 322, and the aperture 336 of the base 330. In the standard configuration, the depth stop 300 is free to slide up and down the morcellator shaft. However, upon positioning in a location where it is desired that the depth stop 300 be secured, the surgeon merely shifts the slide 324 from a first position, upward within the open section 338 toward the plug 316 which fits within the open section. This action tends to rotate the stop lever 322 about its intersection with the spring 326, outside the cross sectional area of the shaft, and effectively reduces the cross sectional area presented to the shaft by the cylindrical section 346 of the stop lever 322. As such, it will be appreciated that a line force is imposed around a portion of the circumference of the shaft by the stop lever 322, effectively securing the depth stop 300.

A fourth embodiment of the invention is provided starting with FIG. 5A, which depicts depth stop 400. Depth stop 400 comprises two components, a base 402 and clamp 404.

As shown in FIG. 5B, the base 402 comprises a domed upper portion 406 with a lumen 408 extending through its central portion. Opposite of the domed upper portion 406 is a circular foot 410. Connecting the domed upper portion 406 and the foot 410 is a split strap 412. It will be appreciated that the lumen 408 extends through the split strap 412 and the foot 410.

The split strap 412 comprises an anchor 414 which provides the actual connection between the domed upper portion 406 and the foot 410. Extending from the anchor 414 are two arms 416, 418 (418 is most clearly shown in FIG. 5C).

Figure 5C:
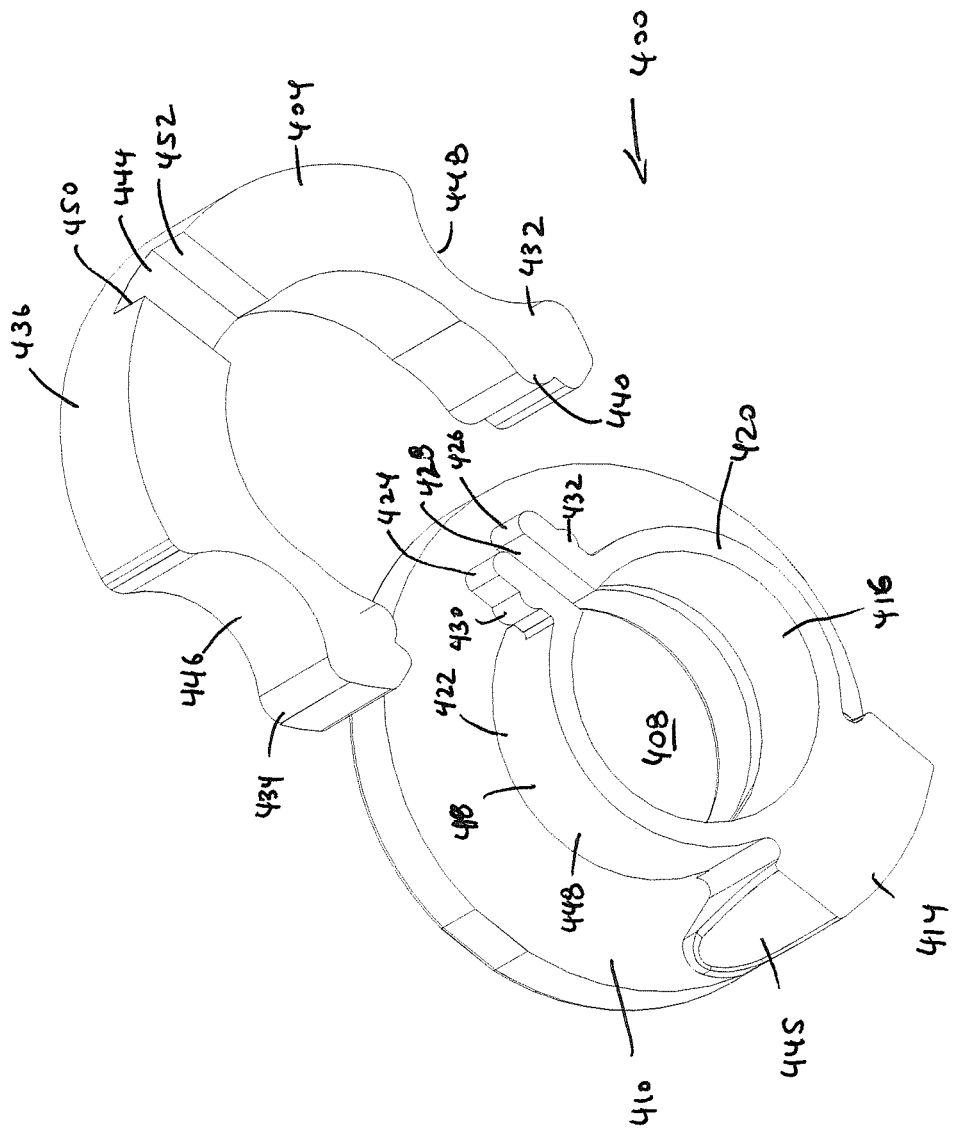
FIG. 5C depicts a cross sectional view of the depth stop of FIG. 5A.

FIG. 5C is a cross sectional view of the depth stop 400. As shown in FIG. 5C, the arms 416, 418 are created as opposing arches 420, 422 forming a portion of the lumen 408. The arches 420, 422 begin at the anchor 414 and terminate with tabs 424, 426 which are spaced apart to leave a gap 428. As will be discussed later, the arches 420, 422 may flex at the anchor to open or close the gap 428. Approximately midway along their respective lengths, the tabs 424, 426 include bulges 430, 432.

Also shown in FIG. 5C is the clamp 404. Clamp 404 is generally shaped as a horse shoe with a pair of open arms 432, 434 and a connector 436. The open arms 432, 434 and connector 436 form an inner surface 438 with cams 440, 442 at its end opposite the connector 436. At the connector 436, the clamp 404 also comprises an aperture 444.

It will be appreciated that in operation, the clamp 404 may be grasped by a gloved surgeon at recesses 446, 448 located approximately centrally on its arms 432, 434. The open end (at the arms 432, 434, opposite the connector 436) of the clamp 404 may then be slid against the outer walls 446, 448 of the arches 420, 422 of the split strap 412, simultaneously spreading the arms 432, 434 of the clamp and squeezing the gap 428 of the split strap. To aid in holding the base 402, the anchor includes grasping regions 445, 447. Continuing pressure on the recesses 446, 448 further cams open the clamp 404 by action of the cams 440, 442 against the outer walls 446, 448 of the arches 420, 422. Upon sufficient excursion of the clamp 404 around the split strap 412, when the cams 440, 442 reach the decreasing radius of the split strap 412, the clamp will "pop" into place forcing the tabs 424, 426 to enter the aperture 444 at the connector 436. The inner walls of the recess 450, 452 cooperate with the bulges 430, 432 to effectively close the gap 428, or at least reduce its size. This decreases the diameter of the lumen 408 in the area of the split strap 412.

In this regard, the base 402 of the depth stop 400 may be placed on the shaft of a surgical instrument, such as a morcellator, by threading the shaft through the lumen 408. The base 402 may then be moved up or down the shaft to a desired stop location. At that location, a surgeon may connect the clamp 404 to the base 402 as discussed above to reduce the diameter of the lumen 408 at the split strap 412 and effectively lock the split strap against the shaft. When it is desired to move the depth stop 400, the surgeon simply removes the clamp 400 by pulling back on the recesses 446, 448 in a manner opposite to assembly while supporting the base at the grasping regions 445, 447.

Figure 6B:
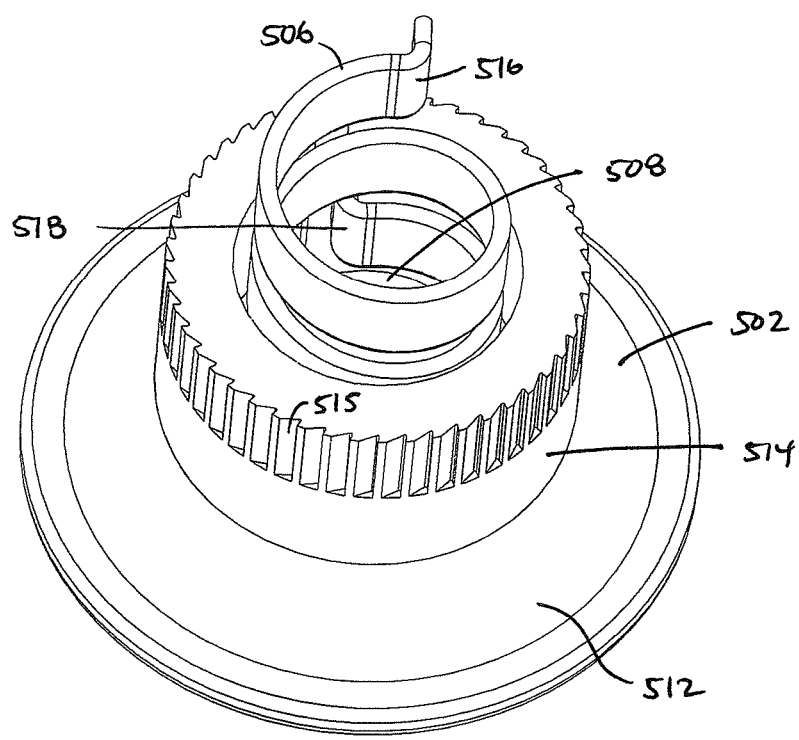
FIG. 6B depicts a perspective view of the inner portion and helical gripper of the depth stop of FIG. 6A.

The fifth embodiment of the present invention is shown initially in FIG. 6A, a perspective view of the depth stop 500. Depth stop 500 comprises three components, an inner portion 502, outer portion 504, and helical gripper 506 (best shown in FIG. 6B).

The inner portion 502 begins, opposite its connection with the outer portion 504, with a mushroom head 506. Although shown in FIG. 6A only at its exit at the outer portion 504, the mushroom head 506 includes a lumen 508 through its central axis 510. The lumen is sized and configured to accept a shaft of a surgical instrument, such as a morcellator. Tapering down from the base 512 of the mushroom head 506 is a cylindrical portion 514. As shown in FIG. 6B, a perspective view of the underside of the inner portion 502, the cylindrical portion 514 ends with a series of sloped recesses 515 around its perimeter. It will be appreciated that these sloped recesses 515 form a portion of a ratchet, as will be discussed.

Figure 6C:
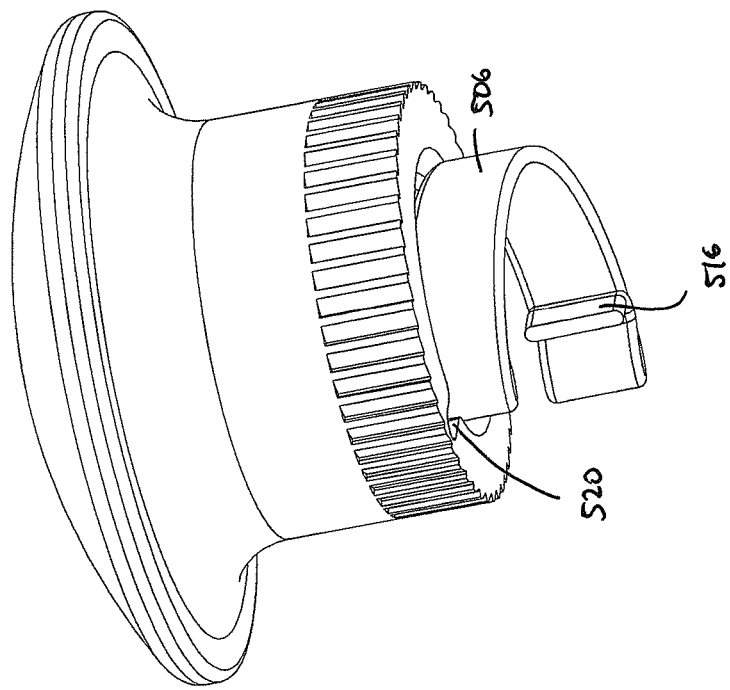
FIG. 6C depicts a second perspective view of the inner portion and helical gripper of the depth stop of FIG. 6A.

Also shown in FIG. 6B is the lumen 508 of the inner portion 502. Within the lumen 508 is the helical gripper 506, which includes at one end a first bent tab 516 and at its second end a second bent tab 518. The second bent tab 518 is fitted within a recess 520, best shown in FIG. 6C, of the lumen 508 of the inner portion 502.

Figure 6D:
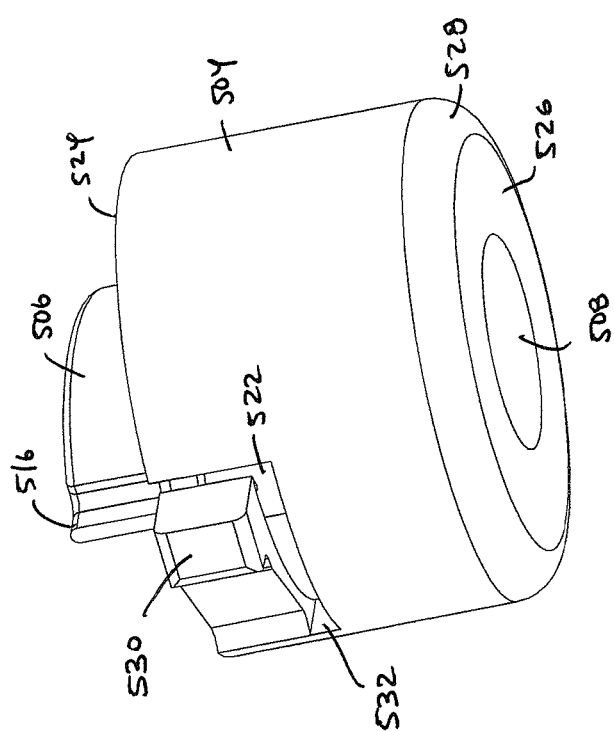
FIG. 6D depicts a perspective view of the outer portion and helical gripper of the depth stop of FIG. 6A.

FIG. 6D depicts a perspective view of the outer portion 504 with helical gripper 506 protruding therefrom. The outer portion 504 is generally cylindrical with a cutout 522 near its upper end 524. At the lower end 526 of the outer portion 504, there is a chamfered edge 528. The lumen 508 passes through the cylindrical outer portion 204 from the lower end 526 to the upper end 524.

Within the cutout 522 is a cantilevered release button 530. As suggested, the release button 530 is cantilevered from an inner wall 532 of the cutout 522 by a pliable arm 534.

FIG. 6E depicts a top perspective view of the outer portion 504. Here, the release button 530 can be seen from its rear 536. On the rear section 536 is mounted a ramp 538. It will be appreciated that when assembled with the inner portion 502, this ramp 538 fits within the one of the series of recesses 515. By virtue of the ramped shape of the ramp 538, and the slope of the recesses 515, the outer portion 504 may rotate relative to the inner portion 502 in the direction of arrow R while the cantilevered release button 530 ratchets from one recess 515 to the next.

Also shown is slot 540. Upon assembly of the depth stop 500, the first bent tab 516 is fitted within the slot 540. Recall that the second bent tab 518 is fitted within recess 520 of the inner portion 502. As the outer portion 504 is rotated relative to the inner portion 502 in the direction of arrow R, the helical gripper 506 is tightened such that its relative cross sectional area is reduced. In the meantime, the outer portion 504 is prevented from rotating in the direction opposite of arrow R by virtue of the ratcheting of the release button 530, and specifically action of the ramp 538 fitting within the one of the series of recesses 515. When it is desired to permit rotation of outer portion 504 in the direction opposite of arrow R, the release button 530 may be lifted to pull the ramp 538 away from, and out of interaction with, the recesses 515. This serves to increase the relative diameter of the helical gripper 506.

It will therefore be appreciated that in use, the depth stop 500 may be fitted on a shaft of a surgical instrument, such as a morcellator. When the depth stop 500 is in a position where it is desired to be affixed, a surgeon may rotate the outer component 504 relative to the inner component 502 in the direction of arrow R to tighten the helical gripper 506 around the shaft. Ratchet action of the ramp 538 and recesses 515 will prevent loosening until such time that the release button 530 is lifted.

Each of the components described in the various embodiments may be configured from a variety of materials. Preferably, such materials are suitable for the surgical arena and have engineering properties suitable for their use. For example, the materials should be capable of repeated use and heat sterilization. Such materials include various metals, polymers, and the like. Items such as spring 326 are preferably metal. Other components, such as the helical gripper 506, may be configured from silicone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A depth stop for a laparascopic instrument having a shaft, where the depth stop comprises:
    a first component having a longitudinal axis and a male connector including a cylindrical structure having an annular wall, the annular wall having an outer surface with a pair of recesses formed in the outer surface and an inner surface defining a first lumen, wherein a geometric centerline of the inner surface of the annular wall is offset from the geometric centerline of the outer surface of the annular wall so that the first lumen is eccentric relative to the outer surface of the annular wall;
    the first component comprising a handle having a bottom portion, wherein the male connector extends from the bottom portion of the handle, and wherein the bottom portion of the handle extends radially outward beyond the male connector;
    a second component adapted to be connected to the first component, the second component having an annular ring with a top portion, the annular ring forming a well having an annular inner wall, a pair of extensions having respective longitudinal axes that project inwardly toward one another from opposite sides of the annular inner wall, a bottom wall and a second lumen formed in the bottom wall, the second lumen having a geometric centerline that is offset from the geometric centerline of the annular inner wall of the well so that the second lumen is eccentric relative to the annular inner wall of the well;

the male connector of the first component being inserted into the well of the second component so that the outer surface of the annular wall of the male connector opposes the annular inner wall of the well with the bottom portion of the handle opposing and extending radially outward beyond the top portion of the annular ring of the second component and with each of the pair of extensions positioned within one of the recesses and so that the first and second eccentric lumens are aligned with one another for receiving the shaft, wherein the first and second components are rotatable relative to one another from an unlocked position to a locked position in which the outer surface of the annular wall of the male connector engages the annular inner wall of the well for shifting the positions of the first and second eccentric lumens relative to one another for imparting a friction force on the shaft that arrests up and down movement of the depth stop along the shaft, wherein in the unlocked position the first and second components of the depth stop are free to move up and down the shaft to a desired position on the shaft and in the locked position the first and second eccentric lumens of the respective first and second components engage the shaft to impart the friction force on the shaft for locking the first and second components of the depth stop in place on the shaft.

2. The depth stop of claim 1, the first eccentric lumen and the second eccentric lumen forming a combined annular space having a first cross sectional area, wherein rotation of the first and second components relative to one another shifts the first and second eccentric lumens relative to one another in a direction that is perpendicular to a longitudinal axis of the shaft to reduce the combined annular space to a second cross sectional area that is less than the first cross sectional area to impart the friction force on the shaft for arresting relative movement of the depth stop along the shaft.

3. The depth stop of claim 1, wherein:
the first component comprises the handle with the cylindrical structure extending from a central location of the bottom portion of the handle, wherein the handle has a mushroom shape; and
the second component having the pair of extensions project radially inwardly from the annular inner wall of the well toward the longitudinal axis of the first component, the pair of extensions being adapted to fit within the recesses when the first component and the second component are connected together for guiding rotation of the first and second components relative to one another.

4. The depth stop of claim 3, wherein each of the recesses comprises a first portion that extends to a lower end of the annular wall of the male connector and a second portion that intersects an upper end of the first portion, that is transverse to the first portion, and that extends beyond both sides of the upper end of the first portion and partially around the central axis of the first component.

5. The depth stop of claim 4, wherein the first component comprises a first notch that is aligned with the first portions of the pair of recesses and the second component comprises a second notch that is aligned with the pair of extensions, wherein the pair of extensions are aligned with the respective first portions of the pair of recesses when the first and second notches are aligned with one another.

6. A depth stop for a laparascopic instrument having a shaft, where the depth stop comprises:
a first component having a central axis and a male connector projecting from an underside thereof, the male connector including an open cylindrical structure forming an annular wall having an outer surface with a pair of recesses formed in the outer surface and an inner surface, the inner surface of the annular wall defining a first lumen that is eccentric relative to the outer surface of the annular wall;
the first component comprising a handle having a bottom portion, wherein the male connector extends from the bottom portion of the handle, and wherein the bottom portion of the handle extends radially outward beyond the male connector;
a second component having an annular ring with a top portion, the annular ring having a well formed therein, the well including an annular inner wall, a pair of extensions that project radially inwardly toward one another from opposite sides of the annular inner wall, a bottom wall and a second lumen formed in the bottom wall that is eccentric relative to the annular inner wall of the well, wherein the first and second components are assembled together so that the male connector is inserted into the well with the bottom portion of the handle opposing and extending radially outward beyond the top portion of the annular ring of the second component and with each of the pair of extensions positioned within one of the recesses and projecting radially inwardly toward the central axis of the first component and with the first and second eccentric lumens aligned with one another for receiving the shaft;
wherein the first and second components are rotatable relative to one another from an unlocked position to a locked position, wherein in the unlocked position the first and second components of the depth stop are free to move up and down the shaft to a desired position on the shaft and in the locked position the inner surface of the annular wall defining the first eccentric lumen and the second eccentric lumen engage the shaft to lock the first and second components of the depth stop in place on the shaft.

7. The depth stop of claim 6, wherein the handle of the first component has a mushroom shape, and wherein in the locked position the inner surface of the annular wall defining the first lumen frictionally engages the shaft and a surface of the second lumen frictionally engages the shaft.

8. The depth stop of claim 6, wherein when the first and second components are rotated relative to one another into the locked position the outer surface of the annular wall of the male connector engages the annular inner wall of the well for shifting the positions of the first and second eccentric lumens relative to one another for imparting a friction force on the shaft that arrests up and down movement of the depth stop along the shaft.

9. The depth stop of claim 8, wherein when the first and second components are rotated relative to one another into the locked position the first and second eccentric lumens are shifted relative to one another in a direction that is perpendicular to a longitudinal axis of the shaft.

10. The depth stop of claim 6, wherein the pair of extensions project radially inwardly from the annular inner wall of the well toward the central axis of the male connector, wherein the pair of extensions are inserted into the recesses for coupling the first and second components together and guiding rotation of the first and second components relative to one another.

11. The depth stop of claim 6, wherein each of the recesses comprises a first portion that extends to a lower end of the annular wall of the male connector and a second portion that intersects an upper end of the first portion, that is transverse to the first portion, and that extends beyond both sides of the upper end of the first portion and partially around the central axis of the first component.

12. The depth stop of claim 11, wherein the first component comprises a first notch that is aligned with the first portions of the pair of recesses and the second component comprises a second notch that is aligned with the pair of extensions, wherein the pair of extensions are aligned with the respective first portions of the pair of recesses when the first and second notches are aligned with one another.

13. The depth stop of claim 6, wherein the pair of extensions have respective longitudinal axes that project radially inwardly toward the central axis of the first component.

14. A depth stop for a laparascopic instrument having a shaft, where the depth stop comprises:
   a first component having a central axis and a male connector with a first eccentric lumen extending therethrough that is adapted to allow the shaft to be fitted therethrough, the male connector having an outer wall having a pair of recesses formed therein that extend around the central axis;
   the first component comprising a handle, wherein the male connector extends from a bottom portion of the handle, and wherein the bottom portion of the handle extends radially outward beyond the male connector;
   a second component having an annular ring with a top portion, the annular ring forming a well with a second eccentric lumen extending therethrough that is adapted to allow the shaft to be fitted therethrough, the well having an annular inner wall and the second component further comprising a pair of extensions that project radially inwardly toward one another from opposite sides of the annular inner wall, wherein the first and second components are assembled together with the male connector inserted into the well with the bottom portion of the handle opposing and extending radially outward beyond the top portion of the annular ring of the second component and with each of the pair of extensions positioned within one of the recesses and projecting radially inwardly toward the central axis of the first component and so that the first and second eccentric lumens are aligned with one another with the shaft passing through the first and second eccentric lumens, and wherein the first and second components rotate relative to one another for shifting the position of the first and second eccentric lumens relative to one another so that an interference surface of the first eccentric lumen frictionally engages the shaft and an interference surface of the second eccentric lumen frictionally engages the shaft to arrest relative movement of the first and second components of the depth stop along the shaft.

15. The depth stop of claim 14, wherein the frictional engagement with the first eccentric lumen is along a curve.

16. The depth stop of claim 14, wherein each of the recesses comprises a first portion that extends to a lower end of the annular wall of the male connector and a second portion that intersects an upper end of the first portion, that is transverse to the first portion, and that extends beyond both sides of the upper end of the first portion and partially around the central axis of the first component.

17. The depth stop of claim 16, wherein the first component comprises a first notch that is aligned with the first portions of the pair of recesses and the second component comprises a second notch that is aligned with the pair of extensions, wherein the pair of extensions are aligned with the respective first portions of the pair of recesses when the first and second notches are aligned with one another.

18. The depth stop of claim 14, wherein the handle of the first component has a mushroom shape, and wherein the pair of extensions have respective longitudinal axes that project radially inwardly toward the central axis of the first component.

\* \* \* \* \*